(12) United States Patent
Kessell

(10) Patent No.: US 6,683,130 B2
(45) Date of Patent: Jan. 27, 2004

(54) METAL OXIDE DISPERSIONS

(75) Inventor: Lorna Margaret Kessell, Northallerton (GB)

(73) Assignee: Imperial Chemical Industries PLC, London (GB)

( * ) Notice: Subject to any disclaimer, the term of this patent is extended or adjusted under 35 U.S.C. 154(b) by 0 days.

(21) Appl. No.: 09/988,773

(22) Filed: Nov. 20, 2001

(65) Prior Publication Data
US 2002/0054999 A1 May 9, 2002

Related U.S. Application Data

(63) Continuation of application No. PCT/GB00/02000, filed on May 25, 2000.

(30) Foreign Application Priority Data

May 25, 1999 (GB) .............................................. 9912002

(51) Int. Cl.$^7$ ................................................. B01F 17/54
(52) U.S. Cl. ........................ 524/588; 524/266; 524/265; 424/401; 516/33; 516/34
(58) Field of Search ................................ 524/265, 266, 524/588; 516/33, 34; 424/401

(56) References Cited

U.S. PATENT DOCUMENTS

| | | | | | |
|---|---|---|---|---|---|
| 5,143,722 | A | * | 9/1992 | Hollenberg et al. | 424/63 |
| 5,216,033 | A | * | 6/1993 | Pereira et al. | 514/844 |
| 5,902,569 | A | * | 5/1999 | Oshima et al. | 424/59 |
| 6,132,739 | A | * | 10/2000 | Leverett | 424/401 |
| 6,197,282 | B1 | * | 3/2001 | Oshima et al. | 424/59 |
| 6,344,186 | B1 | * | 2/2002 | Hansenne et al. | 424/60 |

FOREIGN PATENT DOCUMENTS

| | | |
|---|---|---|
| EP | 0953336 | 11/1999 |
| GB | 2083452 | 3/1982 |

* cited by examiner

*Primary Examiner*—Margaret G. Moore
(74) *Attorney, Agent, or Firm*—Pillsbury Winthrop LLP

(57) ABSTRACT

A dispersion comprises at least 30 per cent by weight of particles of a metal oxide having an average primary particle size of less than 200 nm dispersed in a siloxane fluid dispersing medium and a dispersing agent wherein said metal oxide particles are hydrphoobic, and the dispersing agent is polylkylene oxide/polyalkylsiloxane block copolymer comprising at least 30 per cent by weight of the copolymer of polyalkylsiloxane. The dispersion is particularly suitable for use as an ingredient in sunscreening cosmetics.

20 Claims, No Drawings

METAL OXIDE DISPERSIONS

CROSS-REFERENCE TO RELATED APPLICATIONS

This is a Continuation of International Application No. PCT/GB00/02000 filed May 25, 2000 which designated the U.S. and was published in the English language. The contents of this PCT application are incorporated in their entirety by reference.

This invention relates to dispersions of metal oxides and in particular to dispersions of metal oxides in a silicone dispersing medium wherein certain polyalkylene oxide/ siloxane copolymers are employed as dispersing agents.

Metal oxides such as titanium dioxide, zinc oxide and iron oxides have been employed as attenuators of ultraviolet light in applications such as sunscreens, plastics films and resins. Generally, metal oxides which are useful in these applications have an average primary particle size less than 200 nm. Dispersions of such metal oxides in certain oily media and in water are known and these dispersions have been used to formulate products such as sunscreening creams and lotions. The availability of the metal oxide in the form of a dispersion which is subsequently mixed with other conventional formulation ingredients to prepare a product has been shown to be advantageous in preparing the products.

The use of siloxane based oils in cosmetics has become popular because they can produce an improved skin feel. Hence, metal oxide dispersions in siloxane based dispersing media are desirable. Such dispersions have been difficult to produce.

It is an object of this invention to make available a stable dispersion of metal oxide in a siloxane dispersing medium and a method of producing sunscreening cosmetics based on siloxane fluids.

According to one aspect of the invention, a dispersion comprises at least 30 per cent by weight of particles of a metal oxide having an average primary particle size of less than 200 nm dispersed in a siloxane fluid dispersing medium and a dispersing agent wherein said metal oxide particles are hydrophobic, and said dispersing agent is a polyalkylene oxide/polyalkylsiloxane block copolymer comprising at least 30 per cent by weight of, the copolymer of polyalkylsiloxane.

The polyalkylene oxide/polyalkylsiloxane block copolymer preferably has the formula (1) below

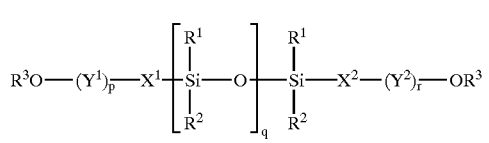

(1)

in which $Y^1$ and $Y^3$ are oxyalkylene moieties, $R^1$ and $R^2$ are alkyl groups, $X^1$ and $X^2$ are alkylene groups, each $R^3$ is, independently, H or an alkyl group and p, q and r are integers chosen such that the proportion of polyalkysiloxane ($-R^1R^2SiO-$) moieties in the copolymer is at least 30 per cent by weight.

As mentioned above, the metal oxide particles used in the invention are hydrophobic. The metal oxide particles may be rendered hydrophobic, for example, by application of a hydrophobic coating on the surface of the metal oxide particles (core particles). The hydrophobic coating may be applied prior to formation of the dispersion, or alternatively in situ, ie during dispersion formation. In addition, as described hereinafter, the particles preferably carry an inorganic coating. Therefore, the term "particles of metal oxide", as used herein is taken to mean the complete particles, i.e. the core particles plus any coating which has been applied.

Preferably the metal oxide used in the invention comprises an oxide of titanium, zinc or iron and most preferably the metal oxide is titanium dioxide in either the rutile or anatase crystal form.

The average primary particle size of the particles of metal oxide is less than 200 nm and where the particles are substantially spherical then this size will be taken to represent the diameter. However, the invention also encompasses particles of metal oxides which are non-spherical and in such cases the average primary particle size refers to the largest dimension. The average particle size which characterises the metal oxides used in the invention is the average size of primary particles, this average size typically being determined by electron microscopy. The size therefore relates to particles of metal oxide which are not aggregated. Frequently, the primary particles consist of single crystals but may also comprise several crystals fused together.

Preferably the average primary particle size of the particles is from 5 to 150 nm and more preferably from 10 to 100 nm when they are substantially spherical. For titanium dioxide particles having an acicular shape the average largest dimension of the primary particles is preferably less than 150 nm and more preferably from 20 to 100 nm.

When the metal oxide is titanium dioxide the particles are preferably acicular in shape and have a ratio of largest dimension to shortest dimension of from 10:1 to 2:1.

When the metal oxide is zinc oxide the particles preferably have an average primary particle size of 30 to 100 nm and very useful products have an average particle size of 30 to 70 nm.

The particles of metal oxide may comprise substantially pure metal oxide but preferably also carry an inorganic coating. For example, particles of titanium dioxide can be coated with oxides of other elements such as oxides of aluminium, zirconium or silicon and a form of acicular titanium dioxide, coated with alumina and silica, which is especially useful in the process of this invention is disclosed in UK Patent GB 2 205 088. Alternatively, particulate metal oxides which carry alumina as the only inorganic oxide coating have also been found to be useful in this invention. The preferred amount of inorganic coating is in the range 4 to 20 per cent by weight, calculated as inorganic oxide with respect to weight of metal oxide core particles. More preferably, the amount of inorganic coating is in the range 5 to 15 per cent by weight, calculated as inorganic oxide with respect to weight of metal oxide core particles. Suitable inorganic coatings can be applied using any appropriate technique and a person skilled in the art will readily be able to apply such a technique. A typical process comprises forming an aqueous dispersion of metal oxide core particles in the presence of a soluble salt of the inorganic element whose oxide will form the coating. This dispersion is usually acidic or basic, depending upon the nature of the salt chosen, and precipitation of the inorganic oxide is achieved by adjusting the pH of the dispersion by the addition of acid or alkali as appropriate.

The particles of metal oxide used to prepare the dispersions of the invention are hydrophobic. Generally, the particles have been treated with a water-repellent material in order to render them hydrophobic. Suitable water-repellent materials include fatty acids, preferably fatty acids containing 10 to 20 carbon atoms, such as lauric acid, stearic acid and isostearic acid, salts of the above fatty acids such as sodium salts and aluminium salts, fatty alcohols, such as stearyl alcohol, and silicones such as polydimethylsiloxane and substituted polydimethylsiloxanes and reactive silicones such as methylhydrosiloxane polymers and copolymers.

The hydrophobic treatment can be applied using any conventional process. Typically, metal oxide core particles (uncoated or with an inorganic coating) are dispersed in water and heated to a temperature in the range 50° C. to 80° C. A fatty acid is then deposited on the metal oxide particles by adding a salt of the fatty acid (e.g. sodium stearate) to the dispersion, followed by an acid. Alternatively, the metal oxide core particles or inorganically coated core particles can be mixed with a solution of the water-repellent material in an organic solvent, followed by evaporation of the solvent. In an alternative embodiment of the invention, the water-repellant material can be added directly to the dispersion of the present invention, during preparation thereof, such that the hydrophobic coating is formed in situ.

Generally, the particles are treated with up to 20 per cent by weight of the water-repellent material, calculated with respect to the coated or uncoated core particles, as appropriate, and preferably with from 6 to 16 per cent by weight of water-repellent material, calculated with respect to coated or uncoated core particles.

The dispersion preferably contains at least 40, more preferably at least 45, and particularly at least 50 per cent by weight of particles of metal oxide.

The metal oxide used in the dispersion of the invention is dispersed in a siloxane fluid dispersing medium. Any suitable siloxane fluid can be used, a principal requirement being cosmetic acceptability. One preferred type of siloxane fluid is a cyclic oligomeric dialkylsiloxane, such as the cyclic pentamer of dimethylsiloxane known as cyclomethicone. Alternative fluids include dimethylsiloxane linear oligomers or polymers having a suitable fluidity and phenyltris (trimethylsiloxy)silane (also known as phenyltrimethicone).

A dispersing agent which is a polyalkylene oxide/polyalkylsiloxane copolymer in which the proportion of polyalkylsiloxane moieties is greater than 30 per cent by weight is used in the dispersion. Preferably, the proportion of polyalkylsiloxane moieties is greater than 40, more preferably greater than 50, and particularly greater than 55 per cent by weight. Usually, the proportion of polyalkylsiloxane moieties is not greater than 80 per cent by weight.

In Formula (1), $R^1$ and $R^2$ are alkyl groups which may be the same or different. Preferably, each of $R^1$ and $R^2$ contain from 1 to 6 carbon atoms and, in particularly preferred dispersing agents, $R^1$ and $R^2$ are both methyl groups. $Y^1$ and $Y^2$ are oxyalkylene groups which preferably contain up to 6 carbon atoms. More preferably, the oxyalkylene groups are oxyethylene or oxypropylene groups. The moiety represented by either or both of $(Y^1)_p$ and $(Y^2)_r$ can comprise a polymeric chain derived from a mixture of alkylene oxides, such as a mixture of ethylene oxide and propylene oxide, wherein $(Y^1)_p$ and/or $(Y^2)_r$ will represent oxyethyleneloxypropylene copolymeric moieties. The groups $X^1$ and $X^2$ are alkylene groups with general formula —$(CH_2)_n$— in which n is preferably 1 to 6 and typically is 3. $R^3$ is H or an alkyl group which, preferably, has up to 6 carbon atoms.

The amount of polyalkylene oxide/polyalkylsiloxane copolymer present is preferably in the range 15 to 40 per cent by weight based on weight of particles of metal oxide. More preferably, the amount is in the range 20 to 30 percent by weight based on weight of particles of metal oxide.

The dispersion may further contain conventional additives suitable for use in the intended application for the dispersion, such as conventional cosmetic ingredients used in sunscreens. Preferably, for maximum flexibility of use, the dispersion consists essentially of the specified ingredients (particles of hydrophobic metal oxide, siloxane fluid dispersing medium and polyalkylene oxide/polyalkylsiloxane copolymer dispersing agent).

The dispersions of the invention are particularly useful for preparing sunscreen products and other compositions intended to attenuate ultraviolet light. For such applications it is desirable that the dispersion strongly attenuates ultraviolet light but is substantially transparent to visible light. In preferred dispersions the particles of metal oxide have a maximum extinction coefficient for light in the ultraviolet range of wavelengths of at least 40 litres per gram per cm. More preferably, the particles of metal oxide in the dispersion have a maximum extinction coefficient in the ultraviolet region of at least 50 litres per gram per cm. Usually the particles of metal oxide in a dispersion which is substantially transparent to visible light will have an extinction coefficient for light in the visible range of wavelengths not greater than 10 litres per gram per cm. Preferably, the particles of metal oxide in the dispersion have an extinction coefficient for light in the visible range of wavelengths not greater than 5 litres per gram per cm.

In a further aspect of the invention a method of preparing dispersions of metal oxides comprising milling with a particulate grinding medium particles of metal oxide in a siloxane fluid dispersing medium and in the presence of a dispersing agent which is a polyalkylene oxide/polyalkylsiloxane block copolymer comprising at least 30 per cent by weight of the copolymer of polyalkylsiloxane, the particles of metal oxide being hydrophobic and being present in an amount such that the proportion of particles of metal oxide in the dispersion is at least 30 per cent by weight and the milling being continued until the primary particles of metal oxide produced have an average particle size less than 200 nm.

A suitable mill which is employed to effect the grinding of the metal oxide product in the dispersing medium is one which uses a particulate grinding medium to grind the product. Typical of such mills are bead mills equipped with one or more agitators and using sand, glass beads or ceramic beads or other particles as the particulate grinding medium. Particularly useful are those mills which operate at a high speed and, depending on the size of mill, a speed in the range 500 to 5000 rev. per minute (r.p.m) is generally suitable. Preferably, mills operating at a speed in the range 800 r.p.m to 3000 r.p.m are used. Agitator mills in which the tip speed of the agitator is up to and can exceed 10 meters per second are of use. If desired the mill can be cooled. Generally, the dispersions are pre-mixed before milling using a high speed stirrer, but, in an alternative process, the dispersing medium is added to the mill initially and then the metal oxide and the dispersing agent co-added to the dispersing medium subsequently. After milling has been carried out for the required time the dispersion is separated from the grinding medium by screening through a narrow gap.

Generally, this method can be used to prepare dispersions possessing the properties of the dispersions of the invention mentioned hereinbefore. In particular, dispersions which strongly attenuate ultraviolet light but are substantially transparent to visible light can be prepared using the method. Frequently, it is possible to adjust the light attenuating profile by adjusting the conditions (e.g. length of time, proportion of grinding medium, concentration of dispersing agent or metal oxide) under which the milling is carried out.

The dispersions of the invention are useful as ingredients for preparing sunscreen compositions, especially in the form of emulsions. Consequently, a further embodiment of the invention comprises a process for preparing an emulsion comprising the steps of (a) preparing a dispersion of particles of metal oxide consisting essentially of at least 30 per cent by weight of hydrophobic particles of metal oxide having a primary particle size of less than 200 nm, a siloxane fluid dispersing medium and a dispersing agent comprising a polyalkylene oxide/polyalkylsiloxane copolymer comprising at least 30 per cent by weight of the copolymer of polyalkylsiloxane, (b) subsequently mixing said dispersion with at least one cosmetically acceptable hydrophobic material to form an oil phase and, (c) subsequently mixing said oil phase with an aqueous phase in the presence of at least one emulsifier in order to produce an emulsion.

The emulsion which is formed may be an oil-in-water emulsion or a water-in-oil emulsion and a skilled person is easily able to select the form of emulsion by selecting appropriate conditions for preparation, such as relative amounts of oil phase and water phase and the amount and chemical composition of the emulsifier(s).

A skilled person is also able to adjust the amounts of ingredients to achieve a desired effect from the product emulsion. When the product is used as a sunscreen the amount of metal oxide present in the final emulsion is typically in the range 0.5 to 30 percent by weight of the emulsion and preferably is in the range 2.0 to 20 per cent by weight of the emulsion. Particularly acceptable emulsions have an oil phase comprising from 10 to 60 per cent by weight of the emulsion, an aqueous phase comprising from 40 to 90 per cent by weight of the emulsion and an emulsifier content in the range 0.5 to 10 per cent by weight of the emulsion.

An alternative suitable process for preparing a sunscreen comprises preparing an emulsion without metal oxide present, using any appropriate technique, and subsequently adding to the emulsion a dispersion of metal oxide particles according to this invention.

In a typical process for preparing an emulsion hydrophilic ingredients of the emulsion are mixed to form an aqueous phase and this phase and the oil phase are separately heated to at least 40° C., preferably to at least 60° C. and more preferably to at least 70° C. These two phases are then mixed under vigorous stirring in the presence of the emulsifier or emulsifiers. Where all the components are liquid, soluble or dispersed in one of the phases at room temperature, it is possible to mix the phases at room temperature without heating the phases. Mixing equipment which has found use for preparing cosmetic creams, lotions etc. is suitable for preparing the emulsions. High shear mixers/homogenisers are particularly suitable but paddle or propeller stirrers can also be employed. Generally, a water-in-oil emulsion is prepared by adding the water phase to the oil phase and an oil-in-water emulsion is prepared by adding the oil phase to the water phase.

The emulsions formed using the aforementioned process may comprise a product suitable for use as a sunscreen without further components. However, other components such as coloured pigments, emollients, humectants, vitamins, moisturisers and preservatives can be added as required. These components may be included within one of the phases during preparation of the emulsion, or, where appropriate, added after the emulsion has been formed.

The metal oxide particles may provide the only ultraviolet light attenuators in an emulsion prepared according to the process of the invention but other sunscreening agents may also be added.

The invention is illustrated by the following non-limiting example.

EXAMPLE

Cyclomethicone (47.5 kg), a polyalkylene oxide/polyalkylsiloxane copolymer (A-B-A type—60 per cent polyalkylsiloxane; 40 per cent polyalkylene oxide (derived from a mixture of ethylene oxide and propylene oxide)) (11.5 kg) and 41.0 kg fine particle titanium dioxide having an average primary particle size of approximately 80 nm (consisting of titanium dioxide coated with approximately 6% alumina and approximately 7% aluminium stearate) were charged to a 120 liter vessel equipped with a high-speed stirrer and pre-mixed for 30 minutes. The mixture was then passed through a horizontal bead mill, operating at approximately 1500 r.p.m. and containing zirconia beads as grinding media. The mixture was passed through the mill and was then returned to the pre-mix vessel and passed through the mill a further three times. The optical characteristics of the resulting dispersion (as determined by UV spectrometry after dilution by a factor of 2000 using n-octanol) are given in Table 1 below, where $\lambda_{max}$ is the wavelength in nm at which maximum attenuation was observed and $E_{max}$, $E_{308}$, $E_{360}$ and $E_{524}$ are the observed extinction coefficients in l/g/cm at $\lambda_{max}$, 308 nm, 360 nm and 524 nm respectively.

TABLE 1

| $\lambda_{max}$ | $E_{max}$ | $E_{308}$ | $E_{380}$ | $E_{524}$ |
| --- | --- | --- | --- | --- |
| 295 | 59.0 | 56.7 | 20.7 | 4.2 |

This dispersion was used to prepare a sunscreen formulation having the following composition.

| INCI Name | % by weight |
| --- | --- |
| Phase A | |
| Cyclomethicone and trimethylsiloxysilicate (Dow Corning 749 Fluid) | 7.5 |
| Dimethicone (Dow Corning 200 Fluid) | 7.5 |
| Cyclomethicone and dimethicone copolyol (Dow Corning 3225c Formulation Aid) | 10.0 |
| Titanium dioxide dispersion produced above | 15.0 |
| Phase B | |
| Glycerin | 4.0 |
| Sodium Chloride | 1.0 |
| Purified water/aqua | 54.5 |
| Preservative | 0.5 |

The ingredients of Phase A were mixed and homogenised by stirring with a Silverson stirrer for 2 minutes. The ingredients of Phase B were mixed and added to Phase A slowly with intensive mixing, followed by stirring with a Silverson mixer for 2 minutes. Finally the mixture was intensively stirred for 30 minutes.

The Sun Protection Factor for the product was determined using the in vitro method of Diffey and Robson, J. Soc. Cosmet. Chem. Vol. 40, pp 127–133, 1989, and a value of 20 was obtained.

What is claimed is:

1. A dispersion comprising at least 30 per cent by weight of particles of a metal oxide having an average primary particle size of less than 200 nm dispersed in a siloxane fluid dispersing medium and a dispersing agent wherein said metal oxide particles are hydrophobic, and said dispersing agent is a polyalkylene oxide/polyalkylsiloxane block copolymer comprising at least 30 percent by weight of the copolymer of polyalkylsiloxane.

2. A dispersion according to claim 1 wherein the polyalkylene oxide/polyalkylsiloxane block copolymer has the formula (1)

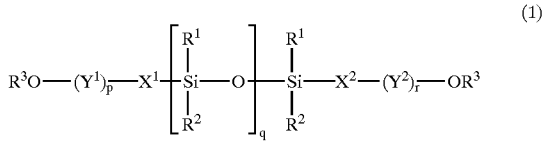

in which $Y^1$ and $Y^2$ are oxyalkylene moieties, $R^1$ and $R^2$ are alkyl groups, $X^1$ and $X^2$ are alkylene groups, each $R^3$ is, independently, H or an alkyl group and p, q and r are integers chosen such that the proportion of polyalkysiloxane (—$R^1R^2SiO$—) in the copolymer is at least 30 per cent by weight.

3. A dispersion according to claim 2 wherein the moieties represented by $(Y^1)_p$ and $(Y^2)_r$ in formula (1) are oxyethylene/oxypropylene copolymeric moieties.

4. A dispersion according to claim 2 wherein the moieties represented by $X^1$ and $X^2$ are both $(CH_2)_3$.

5. A dispersion according to claim 1 wherein the metal oxide is an oxide of titanium, zinc or iron.

6. A dispersion according to claim 1 wherein the particles of metal oxide are titanium dioxide having an acicular shape with an average largest dimension less than 150 nm, and a ratio of largest dimension to shortest dimension in the range 10:1 to 2:1.

7. A dispersion according to claim 1 wherein the particles of metal oxide are zinc oxide with an average primary particle size in the range 30 to 100 nm.

8. A dispersion according to claim 1 wherein the particles of metal oxide carry an organic coating.

9. A dispersion according to claim 1 wherein the particles of metal oxide have been treated with a water-repellent material selected from fatty acids, salts of fatty acids, fatty alcohols, silicones and reactive silicones to render them hydrophobic.

10. A dispersion according to claim 9 wherein the amount of water-repellent material present is up to 20 per cent by weight calculated with respect to the weight of uncoated or inoganically-coated metal oxide particles.

11. A dispersion according to claim 1 wherein the particles of metal oxide are present in an amount of at least 40 per cent by weight with respect to the total weight of dispersion.

12. A dispersion according to claim 1 wherein the siloxane fluid dispersing medium is cyclic oligomeric dialkylsiloxane, a linear dimethyl-siloxane oligomer or polymer or phenyltris(trimethylsiloxy)silane.

13. A dispersion according to claim 1 wherein the polyalkylene oxide/polyalkylsiloxane block copolymer contains greater than 40 per cent by weight of polyalkylsiloxne.

14. A dispersion according to claim 1 wherein the amount of dispersing agent present is in the range 15 to 40 per cent by weight based on the weight of the particles of metal oxide.

15. A dispersion according to claim 1, wherein the particles of metal oxide are present in an amount of at least 45% by weight of the dispersion.

16. A dispersion according to claim 1, wherein the particles of metal oxide are present in an amount of at least 50% by weight of the dispersion.

17. A method of preparing dispersions of metal oxides comprising milling with a particulate grinding medium particles of metal oxide in a siloxane fluid dispersing medium and in the presence of a dispersing agent which is a polyalkylene oxide/polyalkylsiloxane block copolymer comprising at least 30 per cent by weight of the copolymer of polyalkylsiloxane, the particles of metal oxide being hydrophobic and being present in an amount such that the proportion of particles of metal oxide in the dispersion is at least 30 per cent by weight and the milling being continued until the primary particles of metal oxide produced have an average particle size less than 200 nm.

18. A method according to claim 17 wherein the polyalkylene oxide/polyalkylsiloxane block copolymer has the formula (1)

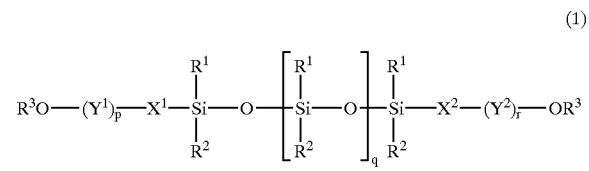

in which $Y^1$ and $Y^1$ are oxyalkylene moieties, $R^1$ and $R^2$ are alkyl groups, $X^1$ and $X^2$ are alkylene groups, each $R^3$ is, independently, H or an alkyl group and p, q and r are integers chosen such that the proportion of polyalkysiloxane (—$R^1R^2SiO$—) in the copolymer is at least 30 per cent by weight.

19. A process for preparing an emulsion comprising the steps of (a) preparing a dispersion of particles of metal oxide consisting essentially of at least 30 per cent by weight of hydrophobic particles of metal oxide having a primary particle size of less than 200 nm, a siloxane fluid dispersing medium and a dispersing agent which is a polyalkylene oxide/polyalkylsiloxane block copolymer comprising at least 30 per cent by weight of the copolymer of polyalkylsiloxane, (b) subsequently mixing said dispersion with at least one cosmetically acceptable hydrophobic material to form an oil phase and, (c) subsequently mixing said oil phase with an aqueous phase in the presence of at least one emulsifier in order to produce an emulsion.

20. A process according to claim 19 in which the emulsion contains from 0.5 to 30 per cent by weight of the particles of metal oxide, from 10 to 60 per cent by weight of oil phase from 40 to 90 per cent by weight of aqueous phase and from 0.5 to 10 per cent by weight of emulsifier.

* * * * *